United States Patent [19]

Dodman et al.

[11] Patent Number: 4,692,451

[45] Date of Patent: Sep. 8, 1987

[54] METHOD FOR PREVENTING STEREOTYPIC BEHAVIOR IN ANIMALS

[75] Inventors: Nicholas H. Dodman, Grafton; Louis Shuster, Brookline, both of Mass.

[73] Assignee: Trustees of Tufts College, Medford, Mass.

[21] Appl. No.: 807,814

[22] Filed: Dec. 11, 1985

[51] Int. Cl.$^4$ .............................................. A61K 31/44
[52] U.S. Cl. ................................................... 514/282
[58] Field of Search ....................................... 514/282

[56] References Cited

U.S. PATENT DOCUMENTS 3,308,791 3/1967 D'Elia ................................. 119/129
3,687,112 8/1972 Hendersen ......................... 119/129

OTHER PUBLICATIONS

Equine Medicine and Surgery, pp. 758-759.
Reverse Tolerance to the Stimulant Effects of Morphine in Horses, Shuster, et al., Pharmacology, vol. 4, No. 5, pp. 233-236.
Effects of Naloxone and Naltrexone on Drug-Induced Hypothermia in Mice, Weiss, et al., Neopharmacology, vol. 23, No. 5, pp. 483-489, 1984.
In Vivo and In Vitro Studies with Agents That Cause Quasi-Morphine Withdrawal Syndromes, Sheldon, et al., Life Sciences, vol. 31, pp. 1699-1702.
The Twitch in Horses: A Variant of Acupuncture, Science, vol. 225, pp. 1172-1174.
Nature's 'fix' article, Leith.

Primary Examiner—Stanley J. Friedman
Attorney, Agent, or Firm—David G. Conlin; Ronald I. Eisenstein

[57] ABSTRACT

A method of treating animals exhibiting stereotypic behavior by administering a therapeutically effective amount of a narcotic antagonist is disclosed. The stereotypic behaviors include cribbing, wind-sucking, head bobbing, head skaking, head nodding, pacing, pawing and stall-walking. A kit for treating this stereotypic behavior is also disclosed.

9 Claims, 3 Drawing Figures

METHOD FOR PREVENTING STEREOTYPIC BEHAVIOR IN ANIMALS

BACKGROUND

This invention relates to a process for a treating stereotypic behavior in animals. This process is particularly useful in treating a specific stereotypic behavior, cribbing, in horses.

The term stereotypic behavior is used herein to describe the repetitive and pointless behavior frequently shown by domesticated animals and animals in captivity. This behavior has been observed, for example, in zoos where a caged bear or lion is seen pacing up and down the cage repetitively for many hours. Horses display a number of different stereotypic behaviors. These include cribbing, wind-sucking, weaving, head bobbing, head shaking, head nodding, pawing, stall walking, etc. Of these behaviors, cribbing and wind-sucking have long been recognized as a serious problem in this species.

Cribbing is often associated with aerophagia. A horse that exhibits this behavior typically grabs an object with its incisor teeth, then arches its neck, and by depressing the tongue and elevating the larynx, pulls backward and upwards and swallows air. As a result of this behavior, which is an acquired habit, the horse suffers many problems, including erosion of the incisor teeth, digestive disturbances, colic, flatulence, and weight loss. Consequently, owners of such horses will go to great lengths to prevent this behavior.

The typical treatment for this behavior includes mechanical prevention by use of throat straps and fluted bits as described for example in U.S. Pat. Nos. 3,687,112 and 3,308,791. Electric shock has been tried as another method of restraint. More radical treatment involves surgical excision of the throat muscles-Forssell's operation (Equine Medicine and Surgery, pages 758–759), or the creation of permanent buccal fistulas.

None of the above methods is entirely satisfactory. The mechanical methods do not prevent cribbing or wind sucking, but merely reduce the frequency by physical restraint. Furthermore, it is not always possible or desirable to maintain use of the mechanical restraint. The surgical measures result in disfigurement, and in any case, a successful outcome is not always guaranteed (The success rate is only about 25%).

It would be desirable to have a simple means of preventing stereotypic behavior that does not result in either mechanical constraint or surgical changes. The treatment is simple to administer and will have long-lasting effects.

SUMMARY OF INVENTION

We have now discovered a method for treating animals exhibiting stereotypic behavior, using narcotic antagonists. A narcotic antagonist is administered in a therapeutically effective amount to an animal exhibiting stereotypic behavior, such as cribbing, wind-sucking, pawing and pacing. The abnormal behavior stops soon are administration of the drug. Animals that could be treated by the use of this method include horses, other domestic mammals, and, caged mammals, such as bears and lions.

DETAILED DESCRIPTION OF THE INVENTION

Figure 1:
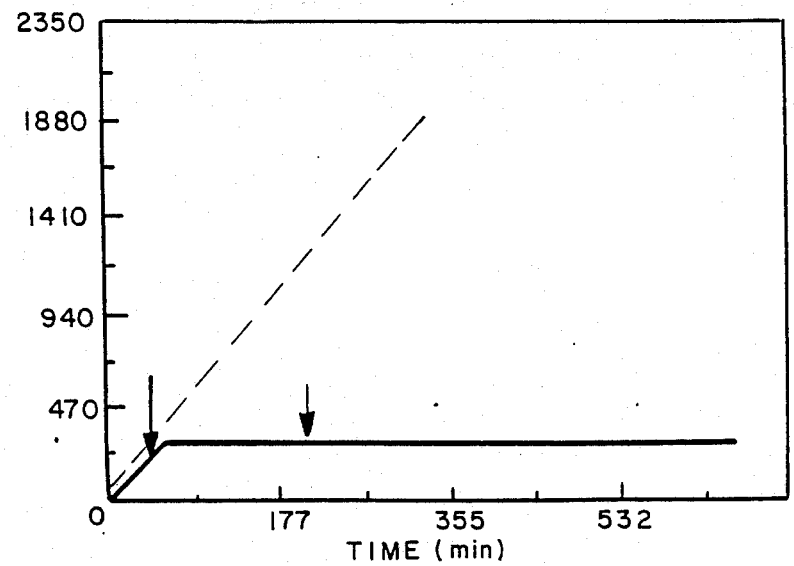
FIG. 1 is a graph contrasting the cumulative amount of cribbing observed over time in an animal treated according to this invention (solid line) and in the same animal when untreated (broken line).

We have discovered that by administering a therapeutic amount of a narcotic antagonist to a domestic mammal such as a horse which exhibits a stereotypic behavior, for example, cribbing, and wind-sucking, head bobbing, head nodding, head shaking, pacing, stall walking, pawing, etc., that the stereotypic behavior is in most instances greatly reduced. It is believed that environmental modification should be combined with the drug administration in order to prevent recurrence of the stereotypic behavior. The environmental modification includes, but is not limited to, moving the animal to a more interesting environment, such as outdoor stalling, providing regular exercise, and providing the company of other animals.

We have found that a variety of different drugs classified as pure narcotic antagonists or partial antagonists are useful in the present invention. Pure antagonists, such as naloxone are preferable, but other drugs which possess varying degrees of antagonist activity may be used. The invention includes, but is not restricted to the following narcotic antogonists:

naloxone,
naltrexone,
nalmefene,
nalorphine,
diprenorphine,
levallorphan,
pentazocine,
metazocine,
cyclazocine,
etazocine, and
peptide drugs with opiate receptor antagonist activity.

Also any drug with demonstrable agonist activity can be imparted with antagonist activity by the addition of an aliphatic group to its nitrogen moiety (e.g., nalorphine is N-allylnormorphine) and the use of such drugs is included within the scope of this invention.

Preferably the narcotic antagonist is selected from the group consisting of naloxone, naltrexone, diprenorophine and nalmefene.

Further, the use of pharmaceutically acceptable acid addition salt of narcotic antagonists is also within the scope of this invention. In general, any suitable inorganic or organic acid may be used to prepare such salt. Examples of suitable inorganic acids are hydrochloric, hydrobromic, sulfuric, nitric, phosphoric, phosphorous, and perchloric acids. Examples of suitable organic acids include tartaric, citric, acetic, succinic, maleic, malic, fumaric, oxalic, ascorbic, benzoic, lactic, palmitic, pamoic, lauric, stearic, oleic, myriatic, lauryl, linoleic and linolenic, acids. However, other organic and inorganic acids which are well known to the person of ordinary skill in the art can be used.

In order for most effective treatment, one would use a drug that can be administered in a form which will have long lasting effect. Thus, although one can use simple intraveneous and oral methods of administration, it would be preferable to use a dosage form that could be administered over a long period of time. This type of administration is well known to the person of ordinary skill in the art. For example, one of ordinary skill can select from intraveneous, intra-muscular, subcutaneous, transdermal, oral, and rectal routes of administration. The dose of the drug to be used is the therapeutically effective amount which will be determined depending upon the particular animal used by techniques well known to the person of ordinary skill in the art. Typically, this would range from about 0.01 mg per kilogram to about 10 mg per kilogram body weight of the animal.

Kits containing therapeutically effective amounts of the narcotic antagonist can be used in the present process for controlling stereotypic behavior. These kits would include sterile and pyrogen-free solutions of the narcotic antagonist sealed in sterile and non-pyrogenic storage vials. The narcotic antagonists include but are not restricted to the following: naloxone; naltrexone; nalmefene, nalorphine; diprenorphine; levallorphan; pentazocine; metazocine; cyclazocine, etazocine and pharmaceutically acceptable acid addition salts thereof. The solutions can be administered by intravenous injections or other techniques well known to the person of ordinary skill in the art.

Preferably, the narcotic antagonist should be injected subcutaneously in the form of a pellet in order to obtain sustained relief for long periods of time. However, other methods of sustained long-term release can be used. These would include plastic patches for transdermal absorption, ambulatory infusion and other techniques.

The following examples are given solely for the purpose of illustration and are not to be considered limitations on the method of the present invention.

EXAMPLE 1

A horse exhibiting cribbing behavior was observed for a control period to establish a base-line for the amount of cribbing. The cribbing rate was expressed in five minute intervals and cumulatively followed for the entire control period. Thereafter, the horse was injected with a narcotic antagonist, such as naloxone, nalmefene, naltrexone and diprenorphine, or a saline solution and observed during a follow up time period. The observer had no knowledge of the material with which the horse is injected, thus resulting in a blind trial. If a horse was injected with saline, it was subsequently injected with the narcotic antagonist and vice-versa.

Horses were injected with either a narcotic antagonist or saline solution intravenously by use of an intravenous catheter or intramuscularly by use of techniques well known to person skilled in the art.

FIG. 1 is a graph plotting the cumulative amount of cribbing observed over time. The dotted line is a fitted regression line based on actual data points for a cribbing horse without treatment (control).

The solid line is a fitted regression line based on actual data points for the same horse on the following day, where the animal received two intramuscular injections of 40 mg nalmefene spaced three hours apart. The use of the narcotic antagonist resulted in the horse being essentially crib free whereas the animal cribbed almost 2000 times on the same period on the previous day.

The slope of the lines represent cribs/minute. The slope of the line for the control day is 5.4. The slope of the line on the following day prior to injection with the narcotic antagonist is similar, 5.2, whereas shortly after injection cribbing has essentially stopped and the slope is 0.045.

Figure 2:
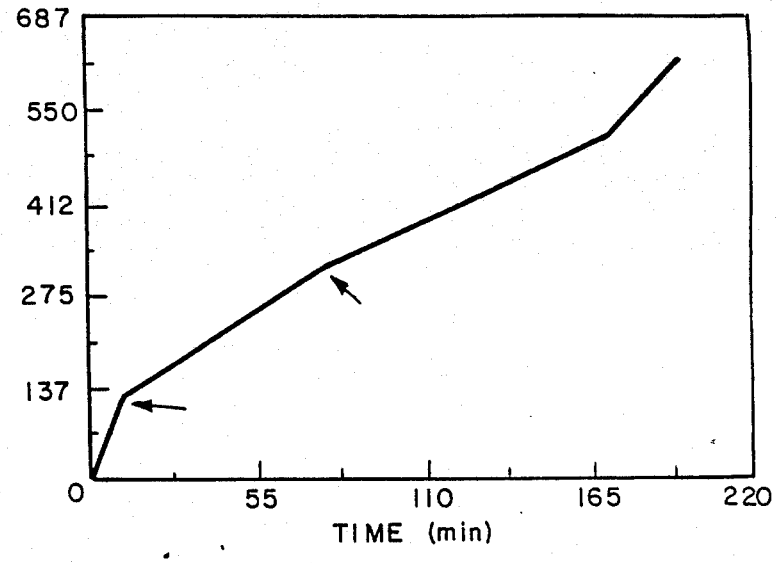
FIG. 2 is a graph showing the effect of cribbing over time in a horse injected with naloxone in accord with the present invention.
Figure 3:
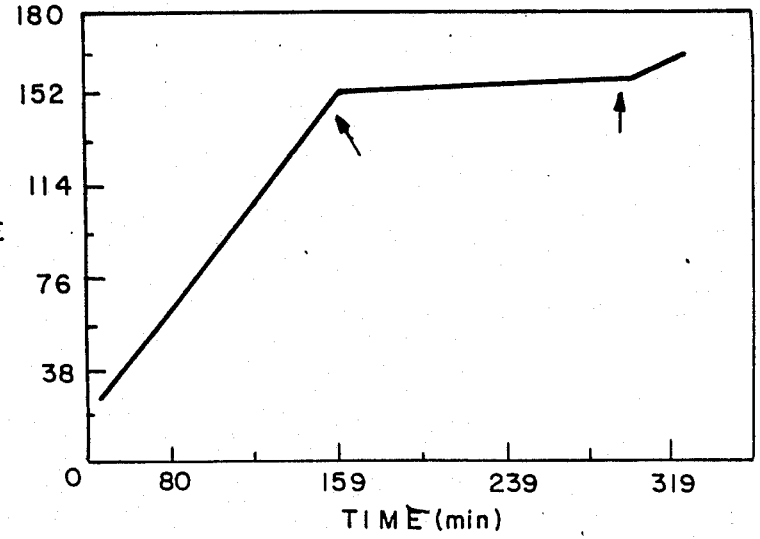
FIG. 3 is a graph showing the effect of cribbing over time in a horse injected with naltrexone in accord with the present invention.

FIG. 2 and FIG. 3 show representative results obtained by use of naloxone and naltrexone injected intravenously into two other horses. In FIG. 2, a horse was injected with 20 mg of naltrexone and this injection was repeated one hour later. Cribbing decreased from a rate of 12.4 cribs per minute to a rate of 2.86 cribs per minute after the first injection and 2.04 cribs per minute following the second injection before the effect of the narcotic antagonist began wearing off. Analogous results are shown in FIG. 3 where 20 mg of naltrexone was injected intra-venously. Cribbing decreased from a rate of 1.08 cribs per minute to 0.005 cribs per minute before the horse was fed sweet feed approximately two and one-half hours later. Sweet feed has a tendency to stimulate cribbing.

Control injections of saline did not alter the cribbing rate of the animals.

EXAMPLE 2

Long term treatment is provided by use of ambulatory infusion pumps (Autosyringe manufactured by Baxter Travenol) set to inject nalmefene at a rate of 10 mg per hour. The pumps are attached to the animal and set up according to directions of the manufacturer.

Table 1 describes a series of treatments in one animal using the methods of the present invention.

TABLE 1

| Treatment | Duration | Cribs per Minute |
|---|---|---|
| Control | 2 hours | 1.9 |
| Control | 7 hours | 5.4 |
| Control | 1 hour | 5.2 |
| Nalmefene, 2 inj. of 40 mg., i.m., at 0 and 3 hours | 10 hours | 0 |
| Control | 5 hours | 8.6 |
| Diprenorphine, 10 mg i.m. | 5 hours | 0.06 |
| Control | 2 hours | 6.3 |
| Nalmefine, osmotic pump S.C., 2 mg/hr. | 2 days | 0 |
| Same osmotic pump | 1 hour (AM) | 1.8 |
| not working anymore | 1 hour (PM) | 2.1 |
| Control | 1 hour | 6.7 |
| Nalmefene, 40 mg i.m. | 4.3 hours | 0 |
| Control | 1 hour | 1.1 |
| 1 g. nalmefene in oil, S.C. | 22 hours | 0 |
| No longer working | 10 minutes | 4.0 |
| No longer working | 1 hour | 1.8 |
| Nalmefene in 4 osmotic pumps, S.C. | 1 hour | 0 |
| Same as above | 1 hour | 0.25 |
| Control | 15 minutes | 1.8 |
| Nalmefene, 50 mg S.C. | 1.5 hours (at up to | 0 |
| Nalmefene, 50 mg S.C. | between 3 and 4 hours | 2.8 |
| Nalmefene, 10 mg 1 hr Continuous infusion S.C. | 5 days | 0 |
| Nalmefene 10 mg per hr continuous infusion, i.v. | 8 days | 0 |
| Off pump (day 9) | 1 hour obs. | 1.2 |
| Off pump (day 10) | 1.5 hours | 8.0 |
| Off pump (day 11) | 1 hour | 2.6 |

It can be seen from Table 1 the use of the narcotic antagonist according to the present invention significantly lowers the rate of a stereotypic behavior, cribbing.

The use of behavioral therapy may be required in some animals in order to result in an effective treatment mechanism. Such therapy techniques are well known to the skilled practioner.

It is expected that the combination of the present treatment with behavioral therapy may allow one to discontinue the use of the narcotic antagonist and not have a recurrence of the stereotypic behavior.

The above-described process has also been used successfully in horses that were hyperactive and engaged in stall walking, pawing and digging.

It will be appreciated that those skilled in the art may make modifications and improvements upon the invention disclosed herein without departing from the spirit and the scope of the invention as described in the claims.

We claim:

1. A method of treating an animal exhibiting stereotypic behavior which comprises administering a therapeutically effective amount of a narcotic antagonist to said animal.

2. The method of claim 1 wherein the stereotypic behavior is selected from the group consisting of cribbing, wind-sucking, head-bobbing, head shaking, head nodding, pacing, pawing and stall-walking.

3. The method of claim 1 wherein the narcotic antagonist is selected from the group consisting of naloxone, naltrexone, nalmefene, nalorphine, diprenorphine, levallorphan, pentazocine, matazocine, cyclazocine, etazocine and a pharmaceutically acceptable acid addition salt thereof.

4. The method of claim 3 wherein the narcotic antagonist is selected from the group consisting of naloxone, naltrexone, diprenorphine and nalmefene.

5. The method of claim 1 wherein the treatment further comprises the use of behavioral therapy.

6. The method of claim 2 wherein the animal is a horse.

7. The method of claim 1 wherein the narcotic antagonist is administered by transdermal absorption.

8. The method of claim 1 wherein the narcotic antagonist is administered in the form of a subcutaneous implant.

9. The method of claim 1 wherein the narcotic antagonist is administered by injection.

* * * * *